United States Patent
Luna

(10) Patent No.: US 11,504,244 B2
(45) Date of Patent: Nov. 22, 2022

(54) ANTERIOR RESURFACING TALAR PLATE

(71) Applicant: Wright Medical Technology, Inc., Memphis, TN (US)

(72) Inventor: Ramon Luna, Arlington, TN (US)

(73) Assignee: Wright Medical Technology, Inc., Memphis, TN (US)

( * ) Notice: Subject to any disclaimer, the term of this patent is extended or adjusted under 35 U.S.C. 154(b) by 0 days.

(21) Appl. No.: 16/085,739

(22) PCT Filed: Mar. 28, 2016

(86) PCT No.: PCT/US2016/024470
§ 371 (c)(1),
(2) Date: Sep. 17, 2018

(87) PCT Pub. No.: WO2017/171707
PCT Pub. Date: Oct. 5, 2017

(65) Prior Publication Data
US 2019/0083273 A1    Mar. 21, 2019

(51) Int. Cl.
*A61F 2/42* (2006.01)
*A61B 17/86* (2006.01)
*A61F 2/30* (2006.01)

(52) U.S. Cl.
CPC ............ *A61F 2/4202* (2013.01); *A61B 17/86* (2013.01); *A61F 2002/3069* (2013.01);
(Continued)

(58) Field of Classification Search
CPC ...... A61F 2/42–4297; A61F 2/38; A61F 2/40; A61F 2/3804–2002/3831; A61F 2/4003;
(Continued)

(56) References Cited

U.S. PATENT DOCUMENTS 3,987,500 A * 10/1976 Schlein ................. A61F 2/4202
623/21.18
4,232,404 A * 11/1980 Samuelson ........... A61F 2/4202
623/21.18

(Continued)

FOREIGN PATENT DOCUMENTS

| JP | 2004135913 A | 5/2004 |
| JP | 2011115440 A | 6/2011 |
| WO | 2008098213 A2 | 8/2008 |
| WO | 2011101699 A1 | 8/2011 |
| WO | 2015175560 A1 | 11/2015 |
| WO | 2016039762 A1 | 3/2016 |

OTHER PUBLICATIONS

International Search Report and Written Opinion issued in connection with International patent application No. PCT/US2016/024470, dated Dec. 20, 2016, 11 pages.

(Continued)

*Primary Examiner* — Alvin J Stewart
(74) *Attorney, Agent, or Firm* — Duane Morris LLP

(57) ABSTRACT

In various embodiments, a surgical plate includes a body extending between a first planar surface and a second planar surface. The body is configured to couple to a first bone. The first planar surface is configured to couple to a first articulation surface. An anterior articulation portion is coupled to the body. The anterior articulation portion includes a third planar surface extending perpendicular to the first and second planar surfaces and a second articulation surface spaced apart from and coupled to the third planar surface. The second articulation surface is configured to articulate with respect to a second bone.

21 Claims, 6 Drawing Sheets

(52) U.S. Cl.
CPC ............... *A61F 2002/30891* (2013.01); *A61F 2002/422* (2013.01); *A61F 2002/4207* (2013.01)

(58) Field of Classification Search
CPC .... A61F 2002/4207; A61F 2002/30995; A61F 2/30988; A61B 17/562; A61B 17/568
See application file for complete search history.

(56) References Cited

U.S. PATENT DOCUMENTS

| | | | | |
|---|---|---|---|---|
| 5,108,444 | A * | 4/1992 | Branemark | A61F 2/4261 623/21.12 |
| 5,326,364 | A * | 7/1994 | Clift, Jr. | A61F 2/4241 606/286 |
| 5,766,259 | A * | 6/1998 | Sammarco | A61F 2/4606 623/21.18 |
| 6,409,767 | B1 * | 6/2002 | Perice | A61F 2/4202 623/21.18 |
| 7,323,012 | B1 * | 1/2008 | Stone | A61F 2/4202 623/21.18 |
| 7,625,409 | B2 * | 12/2009 | Saltzman | A61B 17/15 623/21.18 |
| 7,708,781 | B2 * | 5/2010 | Scheker | A61F 2/3804 623/20.11 |
| 7,892,264 | B2 | 2/2011 | Sanders et al. | |
| 8,105,388 | B2 * | 1/2012 | Palmer | A61F 2/4261 623/21.12 |
| 8,292,966 | B2 * | 10/2012 | Morton | A61B 17/15 623/21.19 |
| 8,303,667 | B2 * | 11/2012 | Younger | A61F 2/64 623/21.18 |
| 8,366,784 | B2 * | 2/2013 | Palmer | A61F 2/4606 623/21.12 |
| 8,597,362 | B2 * | 12/2013 | Shenoy | A61B 17/56 623/20.21 |
| 8,641,770 | B2 * | 2/2014 | Scheker | A61F 2/4241 623/21.16 |
| 8,647,391 | B2 * | 2/2014 | Abidi | A61F 2/4202 128/898 |
| 8,715,362 | B2 | 5/2014 | Reiley et al. | |
| 8,715,363 | B2 * | 5/2014 | Ratron | A61F 2/4606 623/21.18 |
| 8,870,963 | B2 * | 10/2014 | Gonzalez-Hernandez | A61B 17/80 623/19.14 |
| 9,114,016 | B2 * | 8/2015 | Shenoy | A61B 17/56 |
| 9,717,599 | B1 * | 8/2017 | Gorelick | A61F 2/4261 |
| 9,730,797 | B2 * | 8/2017 | Gonzalez-Hernandez | A61F 2/30 |
| 9,757,240 | B2 * | 9/2017 | Gonzalez-Hernandez | A61F 2/4003 |
| 9,757,244 | B2 * | 9/2017 | Sander | A61B 17/1739 |
| 9,962,261 | B1 * | 5/2018 | Scheker | A61F 2/4261 |
| 10,299,939 | B2 * | 5/2019 | Gonzalez-Hernandez | A61F 2/4003 |
| 10,314,712 | B2 * | 6/2019 | Fisher | A61B 17/56 |
| 10,524,919 | B2 * | 1/2020 | Gonzalez-Hernandez | A61F 2/38 |
| 2004/0220675 | A1 * | 11/2004 | Lewis | A61F 2/3804 623/20.11 |
| 2005/0049710 | A1 * | 3/2005 | O'Driscoll | A61F 2/3804 623/20.11 |
| 2006/0149261 | A1 * | 7/2006 | Nilsson | A61F 2/30721 623/18.11 |
| 2007/0055381 | A1 * | 3/2007 | Berelsman | A61F 2/42 623/21.12 |
| 2007/0173947 | A1 * | 7/2007 | Ratron | A61F 2/4606 623/21.18 |
| 2008/0051912 | A1 * | 2/2008 | Hollawell | A61F 2/4225 623/54 |
| 2008/0109081 | A1 * | 5/2008 | Bao | A61F 2/32 623/17.15 |
| 2008/0195217 | A1 * | 8/2008 | Scheker | A61F 2/3804 623/20.11 |
| 2009/0198341 | A1 * | 8/2009 | Choi | A61F 2/30721 623/21.18 |
| 2009/0254189 | A1 * | 10/2009 | Scheker | A61F 2/4261 623/21.11 |
| 2009/0312839 | A1 * | 12/2009 | Scheker | A61F 2/3804 623/20.11 |
| 2009/0318976 | A1 * | 12/2009 | Gabriel | A61B 17/56 606/283 |
| 2010/0121390 | A1 * | 5/2010 | Kleinman | A61B 17/15 606/86 R |
| 2011/0035022 | A1 * | 2/2011 | Linares | A61F 2/30 623/23.39 |
| 2011/0066250 | A1 * | 3/2011 | Palmer | A61F 2/4606 623/21.12 |
| 2011/0093085 | A1 * | 4/2011 | Morton | A61B 17/15 623/21.19 |
| 2011/0230972 | A1 * | 9/2011 | Katrana | A61F 2/3804 623/20.11 |
| 2012/0109322 | A1 * | 5/2012 | Gonzalez-Hernandez | A61F 2/3804 623/19.14 |
| 2012/0185057 | A1 * | 7/2012 | Abidi | A61F 2/4202 623/21.18 |
| 2013/0197655 | A1 * | 8/2013 | Scheker | A61F 2/4241 623/21.16 |
| 2014/0121709 | A1 * | 5/2014 | Gonzalez-Hernandez | A61F 2/4014 606/286 |
| 2014/0121779 | A1 * | 5/2014 | Gonzalez-Hernandez | A61F 2/4261 623/20.12 |
| 2014/0128984 | A1 * | 5/2014 | Jou | A61F 2/4241 623/21.15 |
| 2014/0128985 | A1 * | 5/2014 | Sanders | A61F 2/4225 623/21.18 |
| 2014/0188230 | A1 * | 7/2014 | Rogachefsky | A61F 2/4261 623/18.12 |
| 2014/0316526 | A1 * | 10/2014 | Grotz | A61L 27/54 623/20.17 |
| 2014/0350688 | A1 * | 11/2014 | Michel | A61F 2/4202 623/21.18 |
| 2014/0358242 | A1 * | 12/2014 | Mines | A61F 2/3859 623/20.32 |
| 2014/0358243 | A1 * | 12/2014 | Saffar | A61F 2/4261 623/21.12 |
| 2014/0371867 | A1 | 12/2014 | Schon et al. | |
| 2015/0320567 | A1 * | 11/2015 | Terrill | A61F 2/4202 623/21.18 |
| 2016/0008139 | A1 * | 1/2016 | Siegler | A61F 2/4202 623/21.18 |
| 2016/0338841 | A1 * | 11/2016 | Sander | A61B 17/1739 |
| 2017/0056188 | A1 * | 3/2017 | Dhillon | A61F 2/4202 |
| 2017/0135821 | A1 * | 5/2017 | Anderson | A61B 17/1775 |
| 2017/0151060 | A1 * | 6/2017 | Fisher | A61B 17/56 |
| 2017/0367838 | A1 * | 12/2017 | Cavanagh | A61F 2/4225 |
| 2018/0064544 | A1 * | 3/2018 | Grotz | A61L 27/18 |
| 2018/0353301 | A1 * | 12/2018 | Goldstein | A61B 17/8061 |
| 2019/0038423 | A1 * | 2/2019 | Grotz | A61B 17/562 |
| 2019/0070012 | A1 * | 3/2019 | Leemrijse | A61F 2/4202 |
| 2019/0083273 | A1 * | 3/2019 | Luna | A61B 17/86 |
| 2019/0240036 | A1 * | 8/2019 | Kowalczyk | A61B 17/1775 |
| 2019/0240037 | A1 * | 8/2019 | Gorelick | A61F 2/30749 |
| 2021/0290402 | A1 * | 9/2021 | Chen | A61F 2/3804 |

OTHER PUBLICATIONS

First Office Action issued in connection with corresponding Canadian Patent Application No. 3,017,712, 4 pages, dated Jul. 9, 2019.
Extended Search Report issued in connection with corresponding European Patent Application No. 16897265.1, 8 pages, dated Jul. 6, 2020.

* cited by examiner

ANTERIOR RESURFACING TALAR PLATE

CROSS-REFERENCE TO RELATED APPLICATION

This application is a U.S. national stage application under 35 U.S.C. § 371 of International Application No. PCT/US2016/024470, filed Mar. 28, 2016, the entirety of which is incorporated herein by reference.

TECHNICAL FIELD

This application is generally directed to joint replacement implants, and, more particularly, is generally directed to ankle joint replacement implants.

BACKGROUND

Total ankle replacement systems degrade over time and require replacement. In revision ankle surgery, a total ankle implant is removed and replaced with a new total ankle implant. When the primary implants are removed, a large bone void is left. The bone void is larger than the size of the primary implants removed during the total ankle replacement.

The size of a bone void cannot be determined prior to surgery using current techniques. Current ankle revision systems further require additional cuts and/or modifications of one or more ankle bones during a revision surgery. Primary components must be removed and replaced with augments, which do not provide the same fixed engagement as primary components. Continued bone deterioration can occur and must be corrected during a revision procedure.

SUMMARY

In various embodiments, a surgical plate includes a body extending between a first planar surface and a second planar surface. The body is configured to couple to a first bone. The first planar surface is configured to couple to a first articulation surface. An anterior articulation portion is coupled to the body. The anterior articulation portion includes a third planar surface extending perpendicular to the first and second planar surfaces and a second articulation surface spaced apart from and coupled to the third planar surface. The second articulation surface is configured to articulate with respect to a second bone.

In various embodiments, a surgical kit is disclosed. The surgical kit includes a surgical plate and a bearing element. The surgical plate includes a body extending between a first planar surface and a second planar surface. The body is configured to couple to a first bone. The first planar surface is configured to couple to a first articulation surface. An anterior articulation portion is coupled to the body. The anterior articulation portion includes a third planar surface extending perpendicular to the first and second planar surfaces and a second articulation surface spaced apart from and coupled to the third planar surface. The second articulation surface is configured to articulate with respect to a second bone. The bearing element includes a bearing surface configured to articulate with respect to the second articulation surface of the surgical plate. The bearing element is configured to be coupled to a second bone.

In various embodiments, a surgical method is disclosed. The surgical method includes the steps of resecting an anterior portion of a first bone and coupling a surgical plate to the first bone. The surgical plate includes a body extending between a first planar surface and a second planar surface and configured to couple to a first bone and an anterior articulation portion coupled to the body comprising a third planar surface extending perpendicular to the first and second planar surfaces and anterior articulation surface spaced apart from and coupled to the third planar surface. The anterior articulation surface is configured to articulate with respect to a second bone.

BRIEF DESCRIPTION OF THE FIGURES

The features and advantages of the present invention will be more fully disclosed in, or rendered obvious by the following detailed description of the preferred embodiments, which are to be considered together with the accompanying drawings wherein like numbers refer to like parts and further wherein.

DETAILED DESCRIPTION

Figure 1:
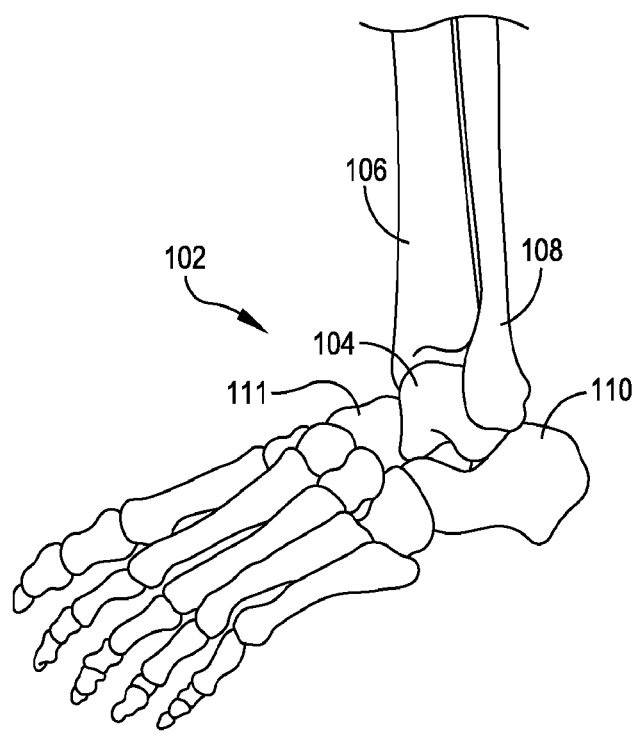
FIG. 1 illustrates an ankle joint, in accordance with some embodiments.

This description of the exemplary embodiments is intended to be read in connection with the accompanying drawings, which are to be considered part of the entire written description. The drawing figures are not necessarily to scale and certain features may be shown exaggerated in scale or in somewhat schematic form in the interest of clarity and conciseness. In the description, relative terms such as "horizontal," "vertical," "up," "down," "top" and "bottom" as well as derivatives thereof (e.g., "horizontally," "downwardly," "upwardly," etc.) should be construed to refer to the orientation as then described or as shown in the drawing figure under discussion. These relative terms are for convenience of description and normally are not intended to require a particular orientation. Terms including "inwardly" versus "outwardly," "longitudinal" versus "lateral" and the like are to be interpreted relative to one another or relative to an axis of elongation, or an axis or center of rotation, as appropriate. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise. When only a single machine is illustrated, the term "machine" shall also be taken to include any collection of machines that individually or jointly execute a set (or multiple sets) of instructions to perform any one or more of the methodologies discussed herein. The term "operatively connected" is such an attachment, coupling or connection that allows the pertinent structures to operate as intended by virtue of that relationship. In the claims, means-plus-function clauses, if used, are intended to cover the structures described, suggested, or rendered obvious by the written description or drawings for performing the recited function, including not only structural equivalents but also equivalent structures.

The present disclosure generally provides a talar implant having an articulation surface sized and configured to allow articulation of a navicular bone. The talar implant includes a first articulation surface and an opposed contact surface. The first articulation surface is sized and configured to articulate with a tibial implant and/or an articulation tray. The first articulation surface comprises a dome shape. The contact surface includes a planar surface configured to couple to a bone and/or a bone plate. In some embodiments, a plurality of fasteners, such as pegs, extend from the contact surface. A second articulation surface extends from an anterior portion of the talar implant. The second articulation surface is sized and configured to articulate with respect to a navicular bone. In some embodiments, the second articulation surface is sized and configured to articulate with respect to an articulation surface coupled to a resected navicular.

Figure 2:
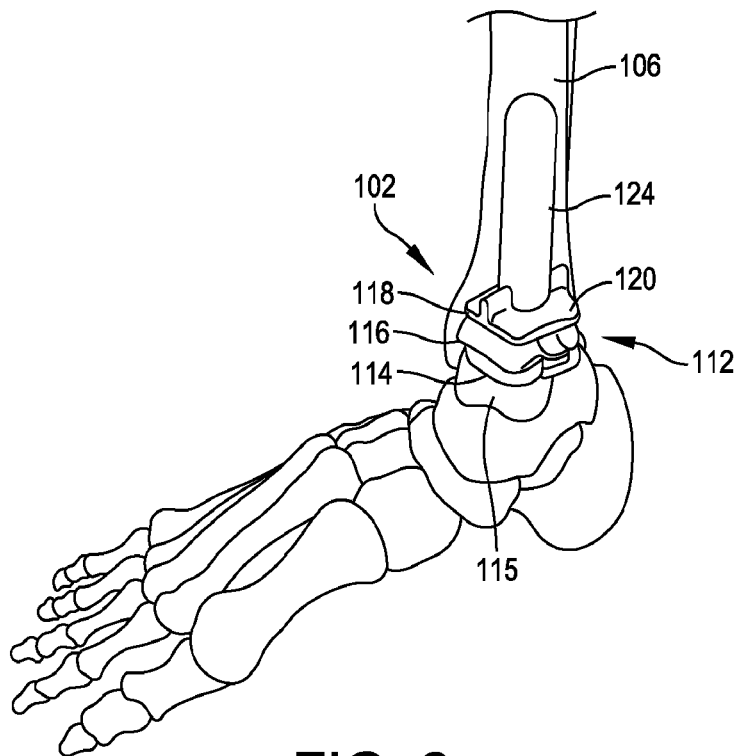
FIG. 2 illustrates a total ankle replacement of the ankle joint of FIG. 1, in accordance with some embodiments.
Figure 3:
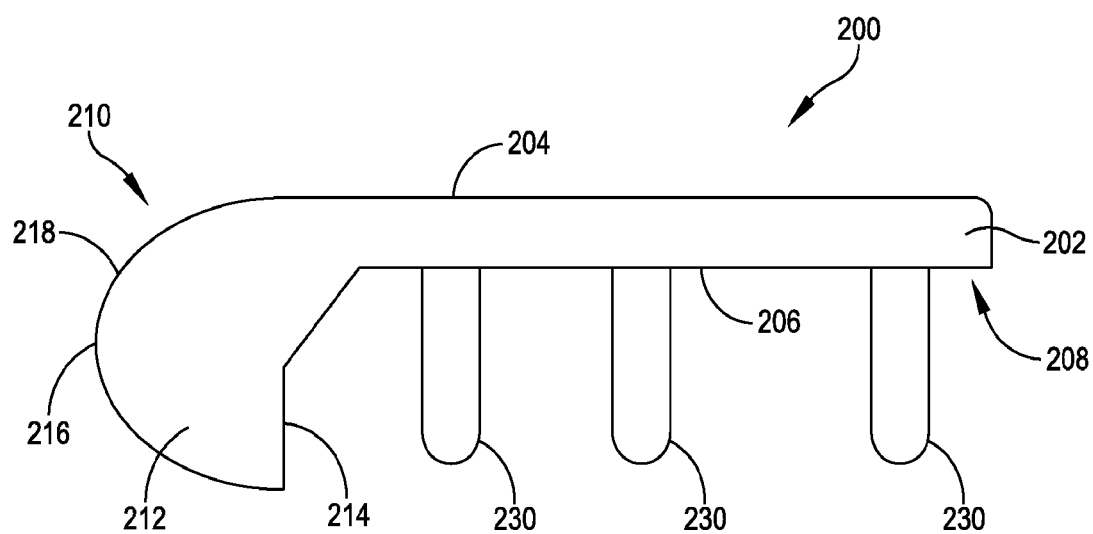
FIG. 3 illustrates a talar plate having an anterior articulation surface, in accordance with some embodiments.

FIG. 1 illustrates an anatomic view of an ankle joint 102. The ankle joint 102 comprises a talus 104 in contact with a tibia 106 and a fibula 108. A calcaneus 110 and a navicular 111 are located adjacent to the talus 104. In total ankle revision and/or primary replacement, the talus 104 and the tibia 106 may be resected, or cut, to allow insertion of primary or revision talar implants and/or tibial implants. FIG. 2 illustrates the ankle joint 102 of FIG. 1 having a total ankle revision system 112 inserted therein.

The total ankle revision system 112 comprises a talar implant 114 and a tibial implant 118. The talar implant 114 comprises a body 115 defining a talar articulation surface 116 (or talar dome). The tibial implant 118 is sized and configured for installation into the tibia 106. The tibial implant 118 comprises a body 119 having an articulation surface 120 and a tibial stem 124 extending into the tibia 106 to anchor the tibial implant 118. The talar joint surface 116 and the tibial joint surface 120 are mutually sized and configured to articulate. The joint surfaces 116, 120 replace the natural ankle joint surfaces, which are removed, to restore a range of motion that mimics the natural joint. One or more holes may be formed in the tibia and/or the talus prior to and during insertion of the tibial implant 118 or the talar implant 114. For example, in some embodiments, a hole is drilled starting in the bottom of the talus, extending through the talus and into the tibia. The hole may comprise, for example, a 6 mm hole configured to receive the stem 124 of the tibial implant 118.

The joint surfaces 116, 120 may be made of various materials, such as, for example, polyethylene, high molecular weight polyethylene (HMWPE), rubber, titanium, titanium alloys, chrome cobalt, surgical steel, and/or any other suitable metal, ceramic, sintered glass, artificial bone, and/or any combination thereof. The joint surfaces 116, 120 may comprise different materials. For example, the tibial joint surface 120 may comprise a plastic or other non-metallic material and the talar joint surface 116 may comprise a metal surface. Those skilled in the art will recognize that any suitable combination of materials may be used.

In some embodiments, replacement of an ankle joint 102 and/or revision of the total ankle replacement system 112 is required due to continued deterioration of one or more bones of the ankle joint 102, such as, for example, due to osteolysis. In some embodiments, a primary talar implant can be replaced with a revision talar implant 114 during a revision procedure. In some embodiments, the revision talar implant 114 includes a talar plate coupled to a talus and configured to couple a talar dome 14 (such as a primary and/or revision talar dome) to the talus during a revision procedure.

In some embodiments, a talar plate 200 includes a body 202 extending between a planar upper surface 204 and a planar lower surface 206. The body 202 is sized and configured to couple to a bone, such as a talus, during a revision procedure. The talar plate 200 includes a posterior portion 208 sized and configured to couple the talar plate 200 to a first bone 260 and an anterior portion 210 sized and configured for resurfacing of an anterior portion of the first bone 260. The posterior portion 208 includes one or more fixation mechanisms for coupling the plate 200 to the first bone 260. In some embodiments, the fixation mechanism includes one or more protrusions 230 (such as pegs or fasteners) extending from the lower surface 206 of the body 202 at a predetermined angle. The protrusions 230 are inserted into holes formed in the bone 260. The holes in the bone 260 can be formed during the revision procedure and/or may be preexisting from a primary total ankle system procedure. In some embodiments, the protrusions 230 can comprise spikes, rounded pegs, fasteners, and/or variable angle pegs or fasteners that can be inserted into the plate 200 at a variable angle.

Figure 5:
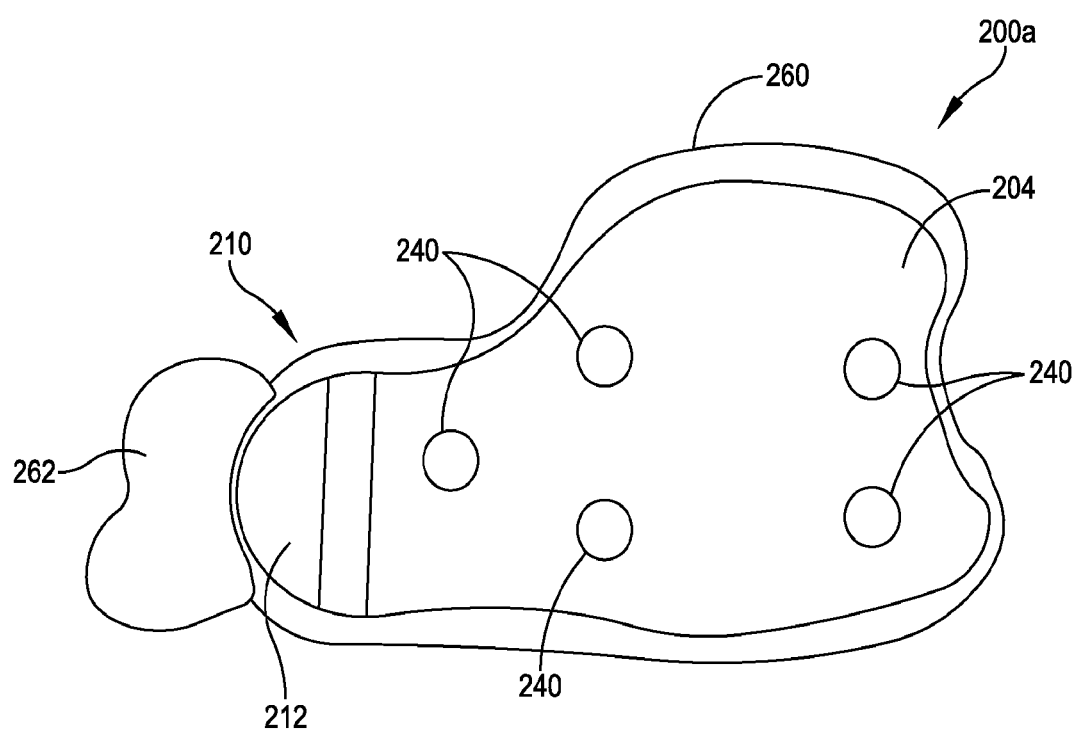
FIG. 5 illustrates a top-down view of a talar plate having a plurality of fastener holes formed therein, in accordance with some embodiments.
Figure 6:
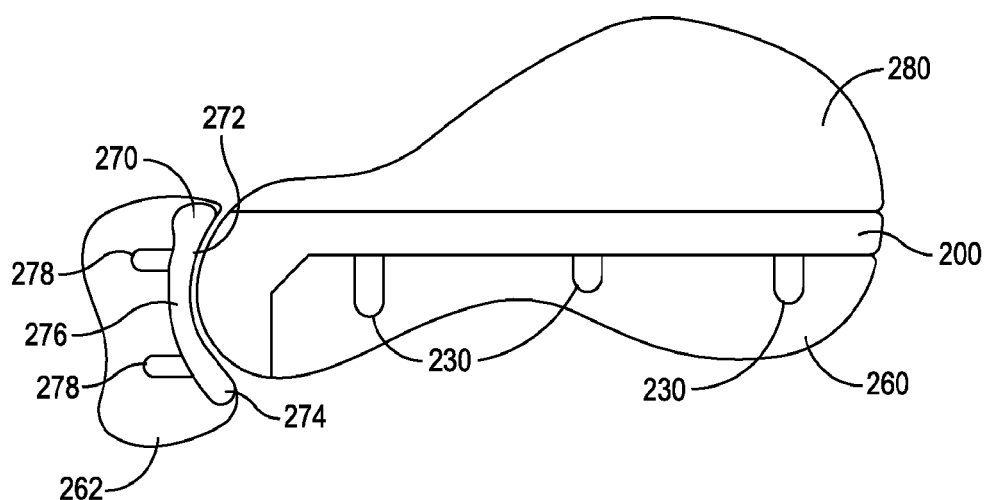
FIG. 6 illustrates one embodiment a talar plate coupled to first bone and a bearing surface coupled to a second bone, in accordance with some embodiments.
Figure 7:
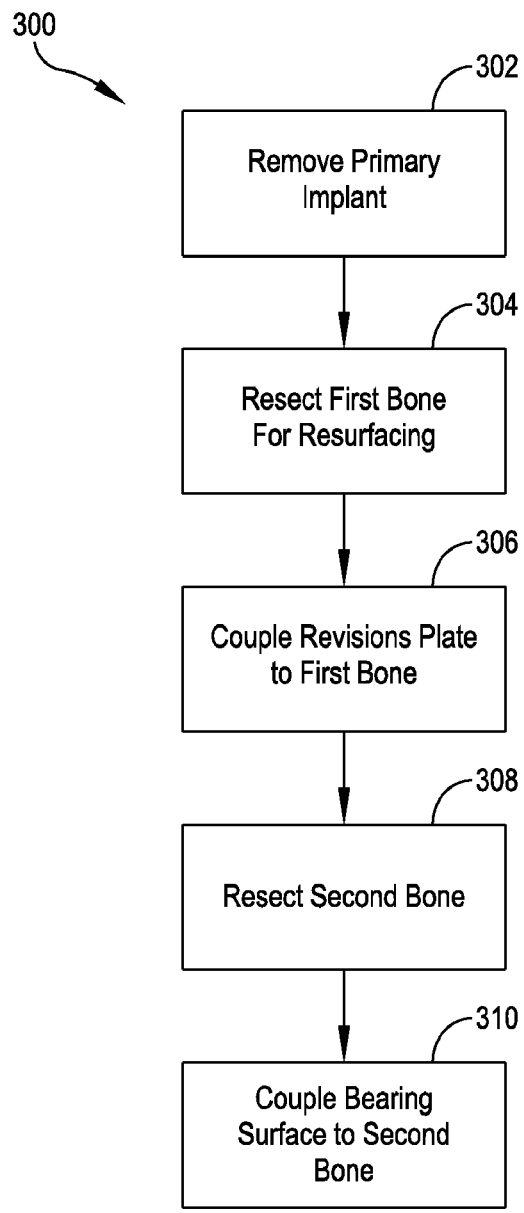
FIG. 7 illustrates a method of resurfacing an anterior talar body, in accordance with some embodiments.

In some embodiments, the fixation mechanism includes one or more fastener holes 240 formed through the body 202 of the plate 200 (see FIG. 5). The fastener holes 240 can comprise any suitable fastener hole, such as, for example, a locking, non-locking, polyaxial, compression, and/or variable angle hole. For example, in some embodiments, the fastener holes 240 comprise Ortholoc 3Di locking holes configured to receive a fastener therethrough at a variable angle and configured to weld and/or lock the fastener by engagement between a threaded head and an inner wall of the fastener hole 240 (e.g., a tappable contact region).

The anterior portion 210 includes an anterior articulation surface 212 having a dome and/or rounded shape. The articulation surface 212 includes a lower surface 214 and an upper surface 216. The lower surface 214 is a planar surface extending perpendicular to the lower surface 206 of the body 202. The upper surface 216 defines a rounded and/or dome-shaped articulation surface 218. The articulation surface 218 is sized and configured to articulate with and/or against a second bone.

Figure 4:
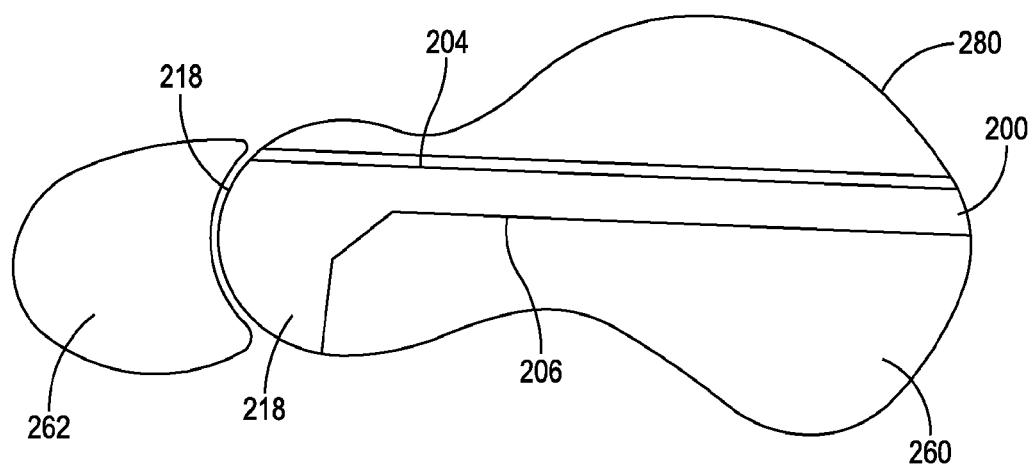
FIG. 4 illustrates the talar plate of FIG. 3 coupled to a bone, in accordance with some embodiments.

In some embodiments, the talar plate 200 is configured to provide anterior talar resurfacing. As shown in FIG. 4, in some embodiments, the talar plate 200 is coupled to a bone 260, such as, for example, a talus. The talar plate 200 can be coupled to the bone 260 by any suitable mechanism, such as, for example, one or more protrusions 230 and/or fasteners. The talar plate 200 is configured to couple to a first articulation surface 280, which may have a size and a shape configured to mimic a natural talar joint surface (e.g., talar dome) configured to articulate with respect to a tibial joint surface. The fasteners can be inserted through fastener holes 240 defined by the body 202 of the plate 200. An anterior portion of the talus is removed during an ankle replacement and/or revision procedure. The talar plate 200 includes an anterior articulation surface 212 sized and configured to articulate with respect to a second bone 262, such as a navicular. The anterior articulation surface 212 has a size and shape configured to mimic an anterior portion of talus such that the anterior articulation surface 212 provides equivalent articulation with respect to the navicular 262. FIG. 5 illustrates a top-down view of a talar plate 200a coupled to the first bone 260.

The anterior articulation surface 212 replaces an anterior portion of the first bone 260 and articulates against the second bone 262. In some embodiments, the anterior articulation surface 212 is configured to replace bone lost due to deterioration and/or removed during a procedure. The anterior articulation surface 212 can comprise any suitable biocompatible material, such as, for example, a metal, a plastic, a composite, and/or any other suitable material. The anterior articulation surface 212 have one or more sizes. During a surgical procedure, a surgeon may select a talar plate 200 having an appropriately sized anterior articulation surface 212 to fill a void and/or replace damaged bone between the first bone 260 and the second bone 262.

In some embodiments, a portion of a second bone 262 is removed and replaced with a bearing element configured to articulate with respect to the anterior articulation surface 212 of the talar plate 200. FIG. 5 illustrates one embodiment of a talar plate 200 coupled to a first bone 260 and a bearing element 270 coupled to a second bone 262. The bearing element 270 comprises a complimentary concave bearing surface 272 configured to match the convex anterior articulation surface 212 of the talar plate 200. In some embodiments, the bearing element 270 comprises a body 274 extending between the complimentary concave surface 272 and an opposing bone-contact surface 276. The body 274 includes one or more fixation mechanisms for coupling the bearing surface 270 to the second bone 262. The one or more fixation mechanism can include one or more pegs 278 and/or fasteners inserted through one or more fasteners defined by the body 274.

With reference now to FIGS. 3-7, a method 300 of anterior talar resurfacing is disclosed. In an optional first step 302, an existing primary talar implant is removed during a revision procedure. The existing talar implant can comprise a talar dome, talar plate, and/or any other suitable talar implant. In other embodiments, the talar plate 200 is installed as part of a total ankle replacement and the first step 302 is replaced with a total ankle replacement method. In a second step 304, a portion of a first bone, such as the anterior portion of a talus, is removed. The amount of bone removed can be determined by the amount of deterioration in the bone, the size of the talar plate and/or implant to be installed, and/or any other suitable factor.

In a third step 306, a talar plate 200 is coupled to the first bone. The talar plate 200 includes a first portion configured to couple the talar plate 200 to a first bone 260, such as a talus. The talar plate 200 can be coupled to the first bone 260 by any suitable coupling mechanism, such as, for example, one or more pegs, spikes, and/or fasteners. The fasteners can comprise variable angle fasteners inserted through one or more holes formed in the body 202 of the talar plate 200. The talar plate 200 is positioned on the first bone 260 such that an anterior articulation surface 212 is positioned to articulate with respect to a second bone 262 adjacent to the first bone 260. In some embodiments, the second bone 262 is a navicular.

In an optional fourth step 308, a portion of the second bone 262 is removed. The portion of the second bone 262 is a portion of the bone configured to articulate with respect to the first bone. The portion of the second bone 262 removed is replaced with a bearing surface 270 in a fifth step 310. The bearing surface 270 is sized and configured to replace the articulation portion of the second bone 262. In various embodiments, the bearing element 270 includes an articulation surface sized and configured to articulate against the anterior articulation surface 212 of the plate 200. The bearing element 270 can include any suitable material such as, for example, a metal material, a plastic material, a composite material, and/or any other suitable material. The bearing surface 270 is coupled to the second bone 262 by one or more fastening mechanisms, such as, for example, one or more pegs, spikes, fasteners, and/or any other suitable fastening mechanism.

Although the devices, kits, systems, and methods have been described in terms of exemplary embodiments, they are not limited thereto. Rather, the appended claims should be construed broadly, to include other variants and embodiments of the devices, kits, systems, and methods, which may be made by those skilled in the art without departing from the scope and range of equivalents of the devices, kits, systems, and methods.

What is claimed is:

1. A surgical plate, comprising:
a body extending between a first planar surface and a second planar surface, the body including at least one protrusion projecting outwardly from the second planar surface through at least one fastener hole that communicates between the first planar surface to the second planar surface to engage a first bone while being oriented at an angle relative to the second planar surface, wherein the first planar surface is sized to couple to a first articulation surface of the first bone and extend an entire length of the body; and
an anterior articulation portion extending from the body, the anterior articulation portion including a third planar surface extending perpendicular to the first and second planar surfaces and a second articulation surface that is dome-shaped and extends directly between the first planar surface and the third planar surface, the second articulation surface to articulate with respect to a third bone.

2. The surgical plate of claim 1, wherein the at least one protrusion projects outwardly at a predetermined acute angle, to couple the body to the first bone.

3. The surgical plate of claim 1, wherein the at least one fastener hole receives a fastener therethrough that is oriented at an obtuse angle relative to the first planar surface.

4. The surgical plate of claim 3, wherein the at least one fastener hole is a variable angle fastener hole.

5. The surgical plate of claim 1, wherein the first articulation surface includes a talar dome.

6. A surgical kit, comprising:
a surgical plate, including:
a body extending between a first planar surface and a second planar surface, the body including at least one protrusion projecting outwardly from the second planar surface through at least one fastener hole that communicates between the first planar surface to the second planar surface to engage a first bone while being oriented at one of an acute and an obtuse angle relative to the second planar surface,
a first articulation surface to articulate with respect to a second bone, wherein the first planar surface extends an entire length of the body to the first articulation surface; and
an anterior articulation portion coupled to the body, the anterior articulation portion including a third planar surface extending perpendicular to the first and second planar surfaces and a second articulation surface extending directly between the first articulation surface and the third planar surface, the second articulation surface to articulate with respect to a third bone; and a bearing element including a bearing surface to articulate with respect to the second articulation surface of the surgical plate while the bearing element is coupled to the third bone.

7. The surgical kit of claim 6, wherein the at least one protrusion projects outwardly from the second planar surface at a predetermined angle, to couple the body to the first bone.

8. The surgical kit of claim 6, wherein the at least one fastener hole extends from the first planar surface to the second planar surface and receives a fastener therethrough that is oriented at an angle relative to the first planar surface.

9. The surgical kit of claim 8, wherein the at least one fastener hole is a variable angle fastener hole.

10. The surgical kit of claim 6, wherein the first articulation surface includes a talar dome.

11. The surgical kit of claim 6, wherein the bearing element includes at least one fixation element extending from a bone contact surface that is opposed to the bearing surface.

12. The surgical kit of claim 6, wherein the first bone is a talus, the second bone is a tibia, and the third bone is a navicular.

13. A method of resurfacing a bone, comprising:
resecting an anterior portion of a first bone;
coupling a surgical plate to the first bone, the surgical plate including a body including at least one protrusion projecting outwardly from a second planar surface through at least one fastener hole that communicates between a first planar surface, which extends an entire length of the body to a first articulation surface, to the second planar surface to engage the first bone while being oriented at least at one of an acute and an obtuse angle relative to the second planar surface, and an anterior articulation portion coupled to the body and including a third planar surface extending perpendicular to the first and second planar surfaces and an anterior articulation surface extending directly between the first planar surface and the third planar surface, wherein the anterior articulation surface articulates with respect to a second bone; and
coupling a posterior articulation surface to the surgical plate.

14. The method of claim 13, wherein prior to resecting the first bone, removing one or more primary components coupled to the first bone of a previous total ankle replacement implant.

15. The method of claim 13, wherein coupling the surgical plate to the first bone includes inserting one or more pegs extending from the second planar surface of the body into one or more channels defined in the first bone.

16. The method of claim 13, wherein
coupling the surgical plate to the first bone includes inserting one or more fasteners at a variable angle through the surgical plate and into the first bone, and the one or more fasteners are coupled to the surgical plate at the variable angle.

17. The method of claim 13, comprising:
resecting an articulation portion of the second bone; and
coupling a bearing element to the second bone, the bearing element including a bearing surface to articulate with respect to the anterior articulation surface of the surgical plate.

18. The method of claim 17, wherein the bearing element is coupled to the second bone by inserting one or more pegs extending from an opposing surface of the bearing element into the second bone.

19. The method of claim 13, wherein the first bone is a talus and the second bone is a navicular.

20. A surgical plate, comprising:
a body including a first surface spaced apart from a second surface, and at least one post projecting outwardly from the second surface through at least one opening communicating between the first surface to the second surface; wherein the at least one opening is oriented through the body to accept the at least one post that is oriented at least at one of an acute and an obtuse angle relative to the second surface to couple the body to a first bone, wherein the first surface is sized to be engaged with a first articulation surface of the first bone and extend an entire length of the body; and
an anterior articulation portion coupled to the body, the anterior articulation portion including a third surface extending perpendicular to the first and second surfaces and a second articulation surface extending directly between the first surface and the third surface, the second articulation surface to articulate with respect to a third bone.

21. A method of resurfacing a bone, comprising:
resecting an anterior portion of a first bone;
coupling a surgical plate to the first bone, the surgical plate including:
a body;
a first surface spaced apart from a second surface, with at least one post projecting outwardly from the second surface through at least one opening communicating between the first surface to the second surface; wherein the at least one opening is oriented through the body to accept the post at an angle relative to the second surface that is at least one of greater than ninety degrees and less than ninety degrees, wherein the first surface is sized to be engaged with a first articulation surface of the first bone and extend an entire length of the body; and
an anterior articulation portion coupled to the body, the anterior articulation portion including a third surface extending perpendicular to the first and second surfaces and a second articulation surface extending directly between the first surface and the third surface, the second articulation surface to articulate with respect to a third bone;
driving a fastener into the at least one opening to engage the body at an angle relative to the second surface to thereby couple the body to the first bone; and
coupling a posterior articulation surface to the surgical plate.

* * * * *